United States Patent [19]

Kijima et al.

[11] Patent Number: 5,316,440

[45] Date of Patent: May 31, 1994

[54] BLOOD PUMP APPARATUS

[75] Inventors: Toshihiko Kijima; Kunio Horiuchi; Hiroyuki Oshiyama, all of Kanagawa, Japan

[73] Assignee: Terumo Kabushiki Kaisha, Tokyo, Japan

[21] Appl. No.: 12,247

[22] Filed: Feb. 1, 1993

Related U.S. Application Data

[63] Continuation-in-part of Ser. No. 880,748, May 8, 1992.

[30] Foreign Application Priority Data

| May 10, 1991 | [JP] | Japan | 3-135943 |
| Sep. 11, 1991 | [JP] | Japan | 3-232031 |
| Feb. 3, 1992 | [JP] | Japan | 4-47962 |

[51] Int. Cl.$^5$ .............................. F01D 5/12
[52] U.S. Cl. ........................ 415/206; 415/900
[58] Field of Search ............... 415/203, 206, 900; 416/223 B

[56] References Cited

U.S. PATENT DOCUMENTS

| 1,406,297 | 2/1922 | Stewart . | |
| 3,107,625 | 10/1963 | Amberg . | |
| 3,487,784 | 1/1970 | Rafferty et al. | 415/900 |
| 3,864,055 | 2/1975 | Kletschka et al. | 415/900 |
| 4,135,253 | 1/1979 | Reich et al. | 415/900 |
| 4,253,798 | 3/1981 | Sugiura . | |
| 4,589,822 | 5/1986 | Clausen et al. | 415/900 |
| 4,606,698 | 8/1986 | Clausen et al. | 415/900 |
| 4,643,641 | 2/1987 | Clausen et al. | 415/900 |
| 4,826,401 | 5/1989 | Clark et al. . | |
| 4,898,518 | 2/1990 | Hubbard et al. | 415/900 |
| 4,984,972 | 1/1991 | Clausen et al. . | |
| 5,118,264 | 6/1992 | Smith | 415/900 |
| 5,145,333 | 9/1992 | Smith | 415/900 |
| 5,147,187 | 9/1992 | Ito et al. | 415/900 |

FOREIGN PATENT DOCUMENTS

| 525787 | 2/1954 | Belgium . | |
| 62417 | 7/1944 | Denmark | 416/223 B |
| 804064 | 2/1951 | Fed. Rep. of Germany | 416/223 B |

OTHER PUBLICATIONS

Artificial Organs, vol. 17, No. 7, 1993, Toshihiko Kijima et al., A Straight Path Centrifugal Blood Pump Concept in the Capiox Centrifugal Pump.

Hydrodynamical and Hemodynamical Evaluation of Rotary Blood Pumps, H. Engelhardt et al., Proceedings of the International Workshop on Rotary Bloodpumps, Vienna, 1988, pp. 76-81.

Primary Examiner—John T. Kwon
Attorney, Agent, or Firm—Frishauf, Holtz, Goodman & Woodward

[57] ABSTRACT

Disclosed is a blood pump apparatus for blood components, comprising a housing forming a substantially cylindrical liquid chamber, an inlet port formed at an upper central portion of the housing and communicating with a source of blood component and the chamber, an outlet port formed in a peripheral portion of the housing and communicating with the chamber, a rotator arranged in the chamber and having an upper cover and a lower shroud, a lower surface of the upper cover being inclined such that an angle $\theta$ formed by the lower surface of the cover and a central axis of the inlet port is an obtuse angle, and a plurality of grooves being formed radially in the upper surface of the shroud, a projection formed at an upper central portion of the shroud and located immediately below the inlet port, bearing rotatably supporting the rotator with respect to the housing, motor for applying a rotational force to the rotator, and a plurality of liquid paths radially formed between the upper cover and the shroud to substantially uniformly distribute blood from a central portion of the rotator to a peripheral portion thereof. Each of the paths has a cross sectional area substantially constant over the entire length region or gradually diminishing in one direction.

28 Claims, 7 Drawing Sheets

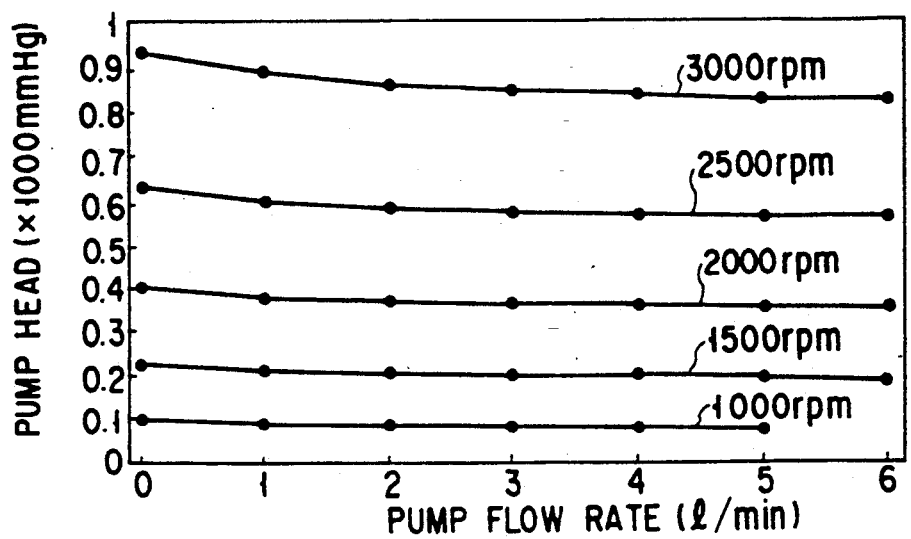
F I G. 14
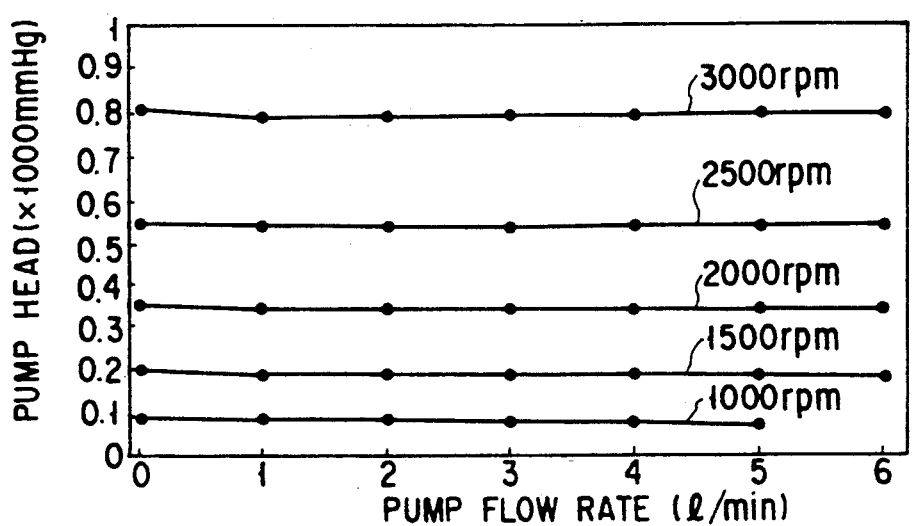
F I G. 15

BLOOD PUMP APPARATUS

CROSS-REFERENCES TO THE RELATED APPLICATIONS

This application is a continuation-in-part of application Ser. No. 880,748 filed on May 8, 1992.

BACKGROUND OF THE INVENTION

1. Field of the Invention

The present invention relates to mainly a blood pump apparatus for transporting a physiological fluid such as blood and, more particularly, to a blood pump apparatus capable of suppressing turbulence of a blood component to be transported and enhancing good pump characteristics at a low speed.

2. Description of the Related Art

Known turbo pump apparatuses for transporting a physiological fluid such as blood or plasma are described in U.S. Pat. Nos. 4,589,822 and 3,864,055. These pumps are turbo pumps for feeding blood using centrifugal forces. The former turbo pump generates the centrifugal force upon rotation of a general open type multi-blade vane assembly, while the latter turbo pump generates the centrifugal force by utilizing a friction force between a plurality of conical rotators.

The most important things for blood transportation are to prevent solid components such as erythrocytes and platelets in the blood from being destroyed and to prevent the blood from coagulating as a result of contact with foreign materials. The most important cause for destruction of the above Solid components is blood turbulence during transpiration. The blood pump disclosed in U.S. Pat. No. 3,864,055 is a pump for applying the centrifugal force to the fluid by the friction force between the plurality of conical rotators. This pump is known as a pump for minimizing turbulence in a blood path between the rotators and hence destruction of solid components (Hydrodynamical and Hemodynamical Evaluation of Rotary Blood Pumps: Inter. Workshop on Rotary Blood Pumps: Vienna. 1988 pp. 76–81).

This blood pump, however, has pump efficiency lower than that of a general pump using vanes. In order to obtain a given pump head, the above blood pump requires a higher speed than that of a vane pump having the same size. For this reason, local heating occurs in a seal portion of a rotating shaft, and the blood around the rotating shaft is denatured and coagulated. In order to obtain the same flow rate as the vane pump having the same size, the blood pump requires a plurality of rotators. Since these plural rotators are housed in the pump housing, the volume of the housing is increased, leading to an increased priming volume, i.e., the amount of blood loaded in the pump housing.

On the other hand, the blood pump described in U.S. Pat. No. 4,589,822 uses an open type multi-blade vane assembly having a large opening at its center to reduce local heating at the seal portion of the shaft, so that the blood speed near the seal portion is increased. In addition, a heat sink structure is added to this pump. In the open type vane pump of this type, however, the blood flow tends to be separated from the vanes, vortex and a counter flow tends to occur between the vanes. So, the blood flow tend to be turbulent, and solid components (e.g., erythrocytes) in the blood tend to be destroyed.

In the conventional pump of this type, erythrocytes are likely to be destroyed (so called hemolysis). Also, the function of the blood platelet tends to be lowered. It follows that the conventional pump of this type is not adapted for use over a long period of time. Incidentally, a high pump head can be obtained in general with a low rotation speed in the case of enlarging the pump housing. However, the enlargement of the pump housing gives rise to an inconvenience that the priming volume of the pump is increased.

SUMMARY OF THE INVENTION

It is an object of the present invention to provide a blood pump apparatus capable of substantially preventing the cells within the blood from being destroyed or preventing the function of the cells from being lowered without increasing the priming amount of the fluid filled in the pump housing and capable of obtaining good pumping characteristics at low rotation speed.

According to an aspect of the present invention, a blood pump apparatus comprises a housing forming a substantially cylindrical liquid chamber, an inlet port formed at an upper central portion of the housing and communicating with a supply source of blood component and the chamber, an outlet port formed in a peripheral portion of the housing and communicating with the chamber, a rotator arranged in the chamber and having an upper cover and a lower shroud, a lower surface of the upper cover being inclined such that an angle $\theta$ formed by the lower surface and a central axis of the inlet port is an obtuse angle, and a plurality of grooves being formed radially in an upper portion of said shroud, a projection formed at an upper central portion of the shroud and located immediately below the inlet port, a plurality of liquid paths radially formed between the upper cover and the shroud to substantially uniformly distribute blood from a central portion of the rotator to a peripheral portion thereof, bearing means rotatably supporting the rotator with respect to the housing, motor means for applying a rotational force to the rotator, wherein each of the plurality of liquid paths is formed so that a cross-sectional area thereof is substantially uniform or reduced.

It is desirable for a lower surface of the upper cover to be inclined such that an angle $\theta$ formed by the lower surface and the central axis of the inlet port is an obtuse angle. It is also desirable for a plurality of grooves to be inclined and radially formed on the upper portion of the shroud. The inclination of the lower surface of the cover allows air (bubbles) which is present in the passages at the time of priming operation to be easily removed out of the inlet. The liquid paths of the particular shape permit decreasing the hemolysis, leading to a further improvement in the pump characteristics.

Further, it is desirable for the outlet to be shaped to meet the condition $L \geq 0.4\,R$, where L is a length of chord of contact with an opening communicating with the chamber, and R is the radius of the chamber. The outlet of the particular shape permits preventing the cells in the blood from being destroyed and also permits preventing the function of the cells from being lowered without increasing the priming volume.

The shape of the liquid path is preferably arcuate or straight.

Each of an upper surface and a lower surface of the liquid path preferably is parallel and crosses an axis of the rotator at an angle falling within the range of about 75° to 90°.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 14 is a graph showing the pump characteristics of the blood pump according to the fourth embodiment of the present invention (second control); and FIG. 15 is a graph showing the pump characteristics of a conventional blood pump.

DETAILED DESCRIPTION OF THE PREFERRED EMBODIMENTS

Various embodiments using blood pumps to which the present invention is applied will be described below.

Figure 1:
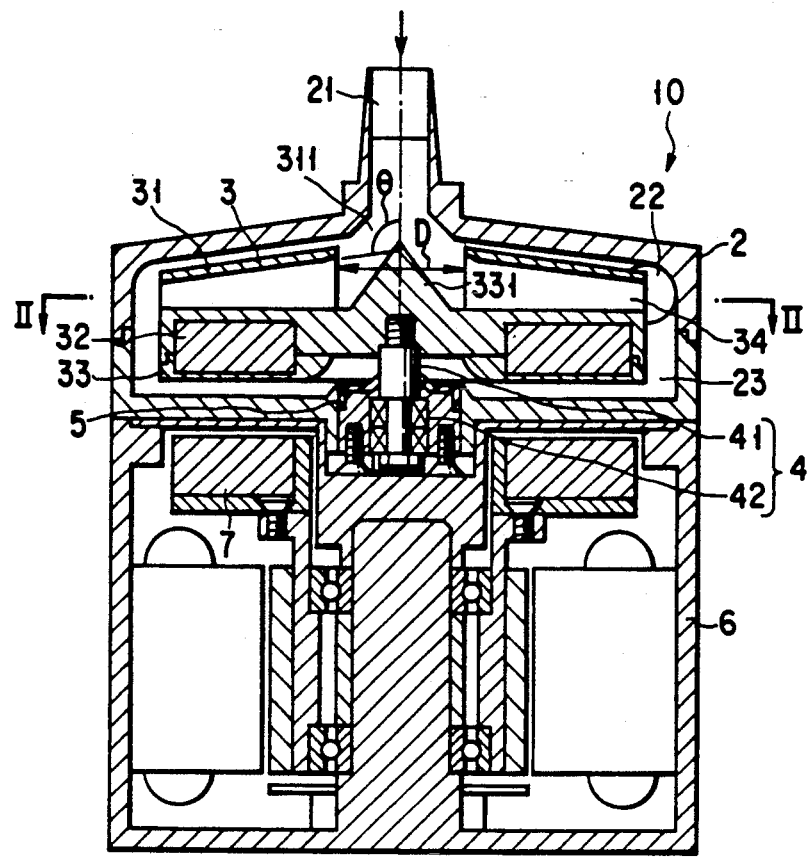
FIG. 1 is a longitudinal sectional view of a blood pump according to the first embodiment of the present invention.
Figure 2:
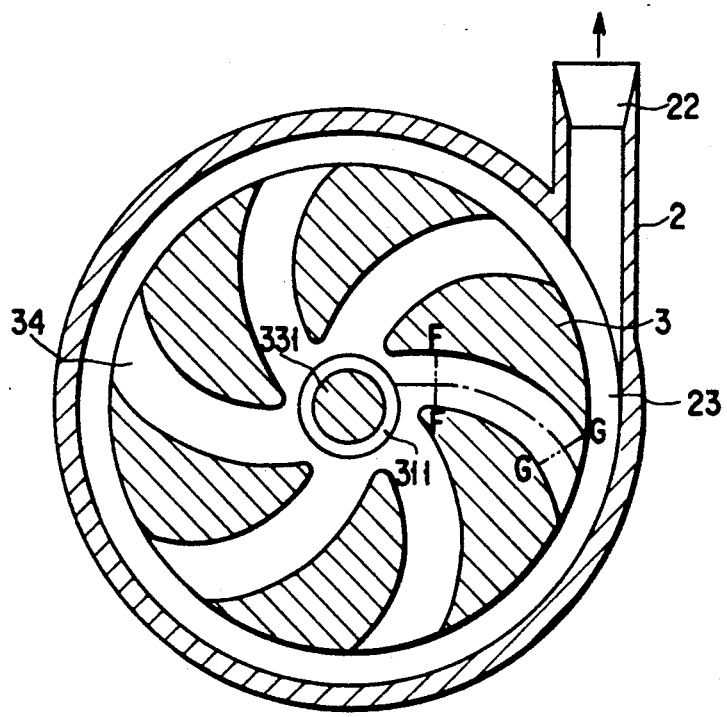
FIG. 2 is a cross-sectional view of the blood pump of the first embodiment when taken along a rotator (II—II in FIG. 1)

As shown in FIGS. 1 and 2, a portion of a blood pump 10 of the first embodiment which guides blood is covered with a housing 2. A blood inlet 21 is formed at the upper central portion of the housing 2 and communicates with a blood reservoir (not shown). An almost cylindrical chamber 23 is formed in the housing 2. A rotator 3 is provided in the chamber 23.

A blood outlet 22 is formed in a peripheral portion of the housing 2, and its flow path is directed to a tangent line of the rotator 3.

Blood is supplied to the housing 2 from the blood inlet 21. A centrifugal force is applied to the blood inside the chamber, and the blood is delivered from the blood outlet 22.

The rotator 3 comprises a cover 31 and a shroud 33 in which a multipolar disk-like driven magnet 32 is embedded. A plurality (six in this embodiment) of liquid paths 34 are radially formed between the cover 31 and the shroud 33. A blood flow inlet 311 is formed in the cover 31 to distribute, the blood supplied from the blood inlet 21 to the liquid paths 34.

More specifically, the blood supplied to the housing 2 is distributed to the liquid paths 34 through the blood flow inlet 311, receives a centrifugal force upon rotation of the rotator 3, and is delivered outside the housing through the blood outlet 22.

Each distribution path 34 has a tubular structure having a rectangular cross-sectional shape and an arcuated shape in its axial direction. The cross-sectional shape of the liquid path 34 is not limited to the illustrated one, but may be circular or a polygonal shape other than a rectangular shape.

Each distribution path 34 is formed so that its cross-sectional area is monotonously decreased along the blood flow within the path. The cross-sectional area along line F—F (FIG. 2) of the path 34 is less than the cross-sectional area along line G—G (FIG. 2) of the path 34. For this reason, the blood flow in the path is accelerated, and the flow tends not to be separated from the walls of paths, thereby suppressing turbulence. With the above arrangement, a sufficiently high pumping ability (pump head) can be obtained at low speed of the pump, without increasing of the blood volume filled in the pump, so that local heating of the blood which is caused by friction of a seal unit 5 (to be described later) can be appropriately suppressed.

Each liquid path 34 is preferably formed so that its upper surface defines an angle $\theta$ falling within the range of about 90° to 105° (96° in the structure in FIG. 1) with respect to the central axis of the rotator 3. In this arrangement, while the blood is filled in the pump, bubbles present in the liquid paths 34 are guided to the upper portion of the housing 2 and are easily removed from the blood inlet 21.

The rate of reduction of the cross-sectional area of each liquid path 34 (i.e.. the ratio of the cross-sectional area of the inlet end of the path to that of the outlet end of the path) is preferably set to be about 50% or less.

The liquid paths 34 are preferably formed at substantially equal angular intervals. The number of liquid paths 34 is not limited to any specific value but can preferably fall within the range of 2 to 12.

A conical projection 331 is formed on the shroud 33 at a position opposite to the blood flow inlet 311 to guide the blood supplied from the blood flow inlet 311 so as to guide the blood to the respective liquid paths 34. The inclined surface of the projection 331 preferably has an angle falling within the range of about 10° to 80° to the central axis. The bottom portion of the projection 331 preferably has a diameter falling within the range of about 1/1 to ¼ the diameter D of the blood flow inlet 311.

A bearing assembly 4 will be described below.

The bearing assembly 4 rotatably supports the rotator 3 in the housing. The bearing assembly 4 comprises a shaft 41 fixed on the shroud 33 and two ball bearings 42 mounted on the inner bottom of the housing 2. The ball bearings 42 and the housing 2 are liquid-tightly separated from each other by the seal member 5.

The seal member 5 is not limited to a lip seal illustrated in FIG. 1, but may be a face seal using an elastic member and a counter face, a mechanical seal using a slidable member made of low friction material and a counter face. or the like.

A sliding bearing or the like may be used in place of the ball bearing 42.

A rotational torque for driving the rotator 3 is transmitted to the driven magnet 32 from a driving magnet 7 coaxially fixed on the rotating shaft of an external motor 6. The rotator 3 is rotated upon rotation of the external motor 6, and the blood supplied from the blood inlet 21 passes through the blood flow inlet 311 of the rotator 3 and then passes through the plurality of liquid paths 34 arranged radially thus receiving the centrifugal force from these paths 34. The blood is delivered from the blood outlet 22. It is possible to arrange the external motor 6 by a flat brushless motor structure in which only a flat stator coil is used and the driven magnet 32 is directly driven by the stator coil.

A detailed arrangement of the blood pump 10 of the first embodiment will be described below.

First Embodiment

Housing

| Material | Acrylic resin |
| --- | --- |
| Inner Diameter of Housing | 84 mm |
| Amount of Filled Blood | 50 cc |
| Inner Diameter of Blood Inlet | 8 mm |
| Inner Diameter of Blood Outlet | 8 mm |

Rotator

| Material | Polycarbonate resin |
| --- | --- |
| Outer Diameter | 74 mm |
| Inner Diameter of Blood Flow Inlet | 19 mm |
| Number of Liquid Paths (radially arranged at equal angular intervals) | 6 |
| Cross-sectional Area of Inlet Opening of Liquid Path | 50 mm$^2$ |
| Cross-sectional Area of Outlet Opening of Liquid Path | 33 mm$^2$ |
| Angle $\theta$ between Lower Surface of Cover and Central Axis of Inlet Port | 96° |
| Angle between Inclined Surface of Projection and Central Axis | 45° |
| Diameter of Bottom Portion of Projection | 15 mm |
| Driven Magnet | 6-pole magnetized ferrite magnet (outer diameter: 70 mm; inner diameter: 32 mm; and thickness: 8 mm) |

External Drive Unit

| Motor | 90 W brushless DC motor |
| --- | --- |
| Driving Magnet | 6-pole magnetized ferrite magnet (outer diameter: 70 mm; inner diameter: 32 mm; thickness: 10 mm; and Distance from Driven magnet 8.5 mm) |

First Control

A blood pump model BP80 (available from Biomedicus Corp.) described in U.S. Pat. No. 3,864,055 was used. The amount of blood filled in this blood pump was 88 cc.

Measurement of Pump Speed

These pump apparatuses were operated using 1.8 l of blood having a hematocrit rate of 43 l as a liquid to be transported at a pump head of 400 mmHg and a flow rate of 3 l/min. The speed of the blood pump of the first embodiment at this operating point was 2,370 rpm, while the speed of the blood pump of the comparative example at above operating point was 2,900 rpm. The amount of blood filled in the blood pump of the present invention was greatly reduced as that of the comparative example. Therefore, the blood pump of the first embodiment was confirmed to be operable at low speed (lower than that of the conventional pump) to obtain the same pressure head.

Measurement of Hemolytic Rate

These pump apparatuses were operated using 1.8 l of blood having a hematocrit rate of 43 l as a liquid to be transported at a pump head of 400 mmHg and a flow rate of 3 l/min, and hemolytic rates (i.e., free hemoglobin concentration in the blood) over time were measured.

Figure 3:
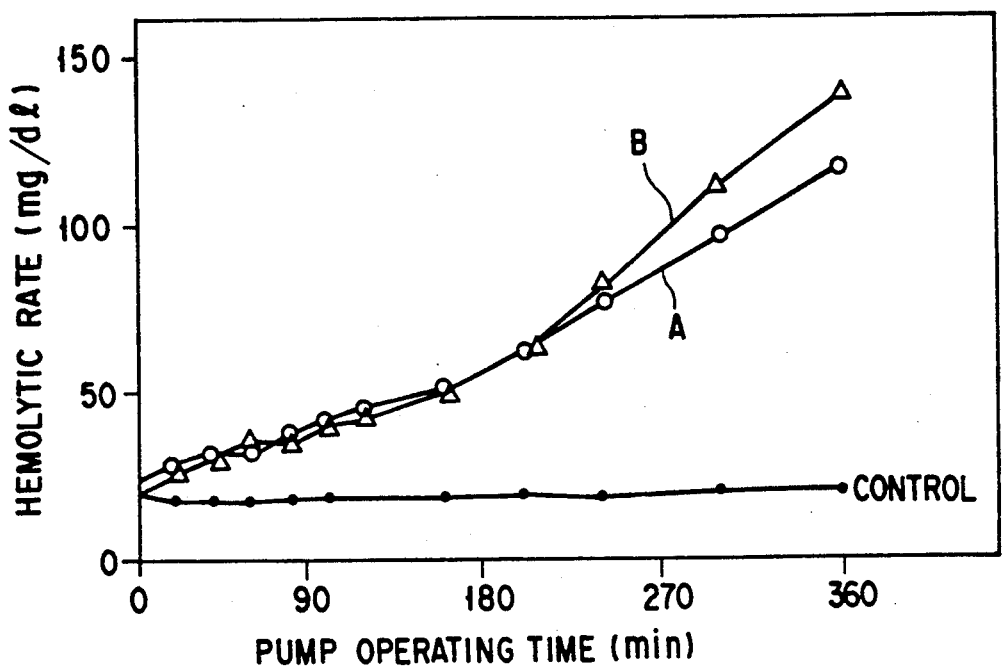
FIG. 3 is a graph showing hemolytic characteristics of the blood pump of the first embodiment and a conventional blood pump (first control)

FIG. 3 is a graph showing measurement results of the first embodiment and the conventional pump in which the pump operating time is plotted along the abscissa and the hemolytic rates are plotted along the ordinate.

The first control represented by dots in FIG. 3 represents a hemolytic rate of the blood which has not yet been transported. Curve A (blank circles) represent the result using the pump of the first embodiment, and curve B (blank triangles) represent the result using the conventional pump.

As is apparent from FIG. 3, the blood pump of the first embodiment of the present invention was confirmed to have almost the same low hemolytic rate as that of the conventional pump.

Figure 4:
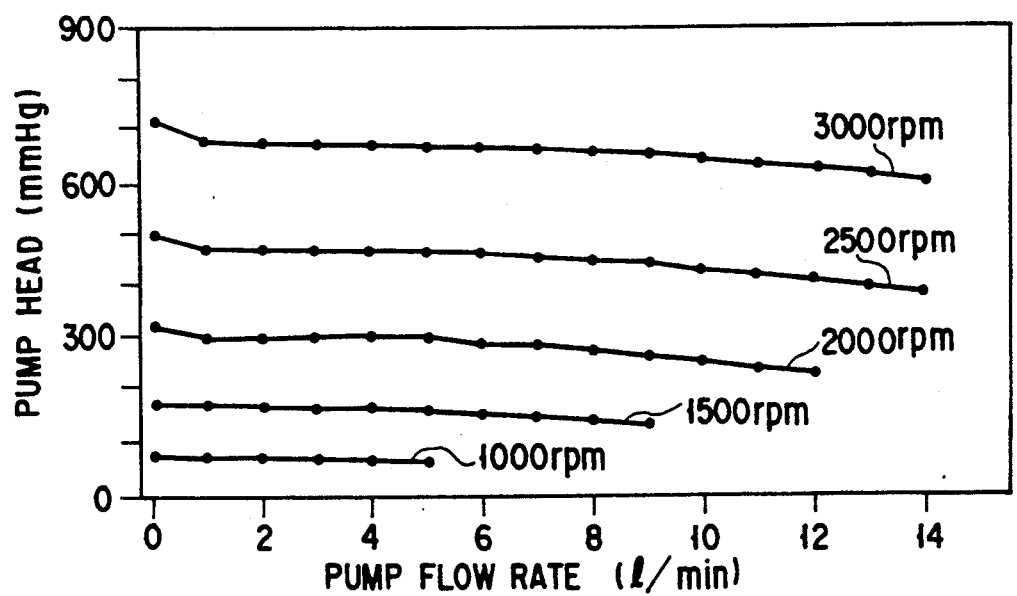
FIG. 4 is a graph showing pumping characteristics of the blood pump of the first embodiment.

FIG. 4 is a graph showing the test results of pumping characteristics of the first embodiment when the pump speed is changed in the range of 1.000 to 3,000 rpm. The pump flow rates are plotted along the abscissa in FIG. 4, and the pump heads are plotted along the ordinate.

A blood pump according to the second embodiment will be described with reference to FIGS. 5 and 6.

The same reference numerals as in the first embodiment denote the same parts in the second embodiment, and a detailed description thereof will be omitted.

A pump 50 of the second embodiment is substantially the same as the pump 10 of the first embodiment, except that blood paths 54 are straight and have constant cross-sectional areas along the blood flow in the paths. With the above arrangement, as compared with the pump 10 in the first embodiment, the amounts of blood filled in the distribution paths can be almost equal to each other, and better pump characteristics can be obtained. In addition, each blood path 54 is formed such that an angle $\theta$ between the central axis of a rotator 51 and that of the paths 54 is set to be 100°.

A detailed arrangement of the blood pump 50 of the second embodiment will be described below.

Second Embodiment

Housing

| Material | Acrylic resin |
|---|---|
| Inner Diameter of Housing | 84 mm |
| Amount of Filled Blood | 47 cc |
| Inner Diameter of Blood Inlet | 8 mm |
| Inner Diameter of Blood Outlet | 8 mm |

Rotator

| Material | Polycarbonate resin |
|---|---|
| Outer Diameter | 74 mm |
| Inner Diameter of Blood Flow Inlet Flow Inlet | 19 mm |
| Number of Liquid Paths (radially arranged at equal angular intervals) | 6 |
| Cross-sectional Area of Inlet Opening of Liquid Path | 32 mm² (IH 4 mm × IW 8 mm) |
| Cross-sectional Area of Outlet Opening of Liquid Path | 32 mm² (OH 4 mm × OW 8 mm) |
| Angle θ between Central Axis of Liquid Path and Central Axis of Inlet Port | 100° |
| Angle between Inclined Surface of Projection and Central Axis | 45° |
| Diameter of Bottom Portion of Projection | 10 mm |
| Driven Magnet | 6-pole magnetized ferrite magnet (outer diameter: 70 mm inner diameter: 32 mm; and thickness: 8 mm) |

External Drive Unit

The same as in the first embodiment.

Figure 7:
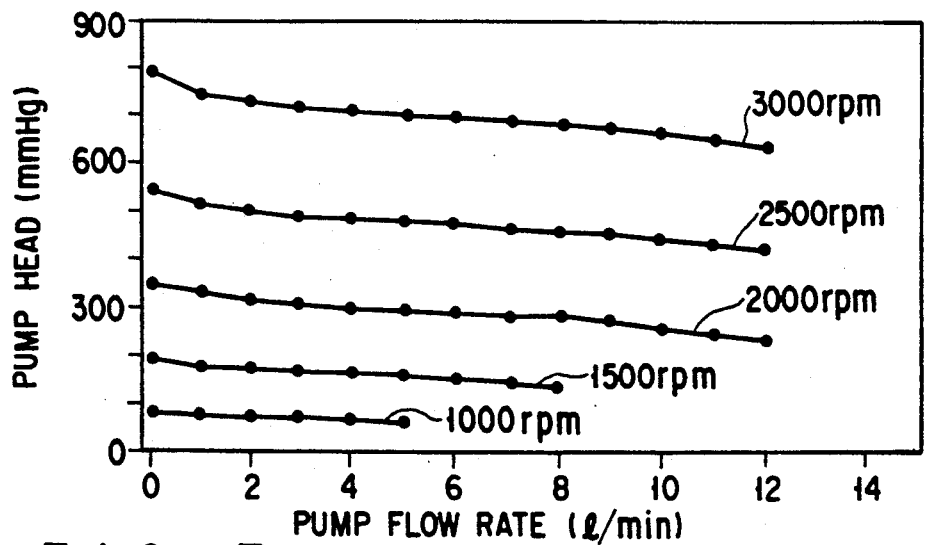
FIG. 7 is a graph showing pumping characteristics of the blood pump of the second embodiment.

FIG. 7 is a graph showing the test results of pumping characteristics of the second embodiment when the pump speed is changed in the range of 1,000 to 3,000 rpm. The pump flow rates are plotted along the abscissa in FIG. 7, and the pump heads are plotted along the ordinate. The pump characteristics were measured using a glycerin solution, viscosity of 4 c.p.

Figure 8:
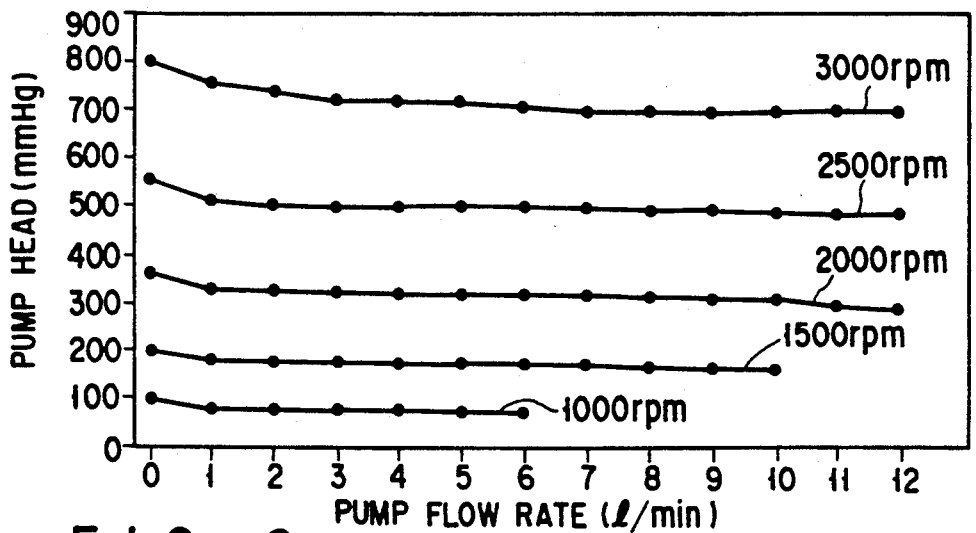
FIG. 8 is a graph showing pumping characteristics of the blood pump of the third embodiment.
Figure 11:
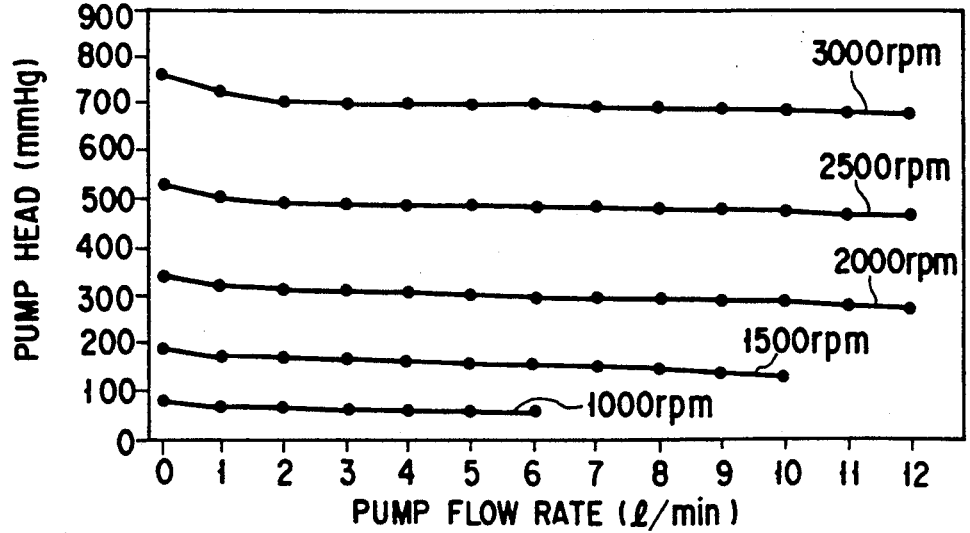
FIG. 11 is a graph showing pumping characteristics of the blood pump of the third embodiment.

A physiological saline at a temperature of 25° C. was transported using two kinds of the blood pumps 70 of the third embodiment, and their pumping characteristics were measured. The measurement was performed by changing the pump speeds and the pump flow rates. The results are shown in FIG. 8 and FIG. 11. Liquid paths of third embodiment of which results shown in FIG. 8 are straight as same as the second embodiment. Liquid paths of third embodiment of which results shown in FIG. 11 are spread at a gradient of about 1° along the blood flow. As is apparent from FIGS. 8 and 11, both of two kinds of blood pumps 70 exhibited good pump characteristics.

FIG. 8 is a graph showing the test results of pumping characteristics of the third embodiment when the pump speed is changed in the range of 1,000 to 3,000 rpm. The pump flow rates are plotted along the abscissa in FIG. 8, and the pump heads are plotted along the ordinate. The pumping characteristics were measured using a physiological saline at a temperature of 25° C.

Figure 9:
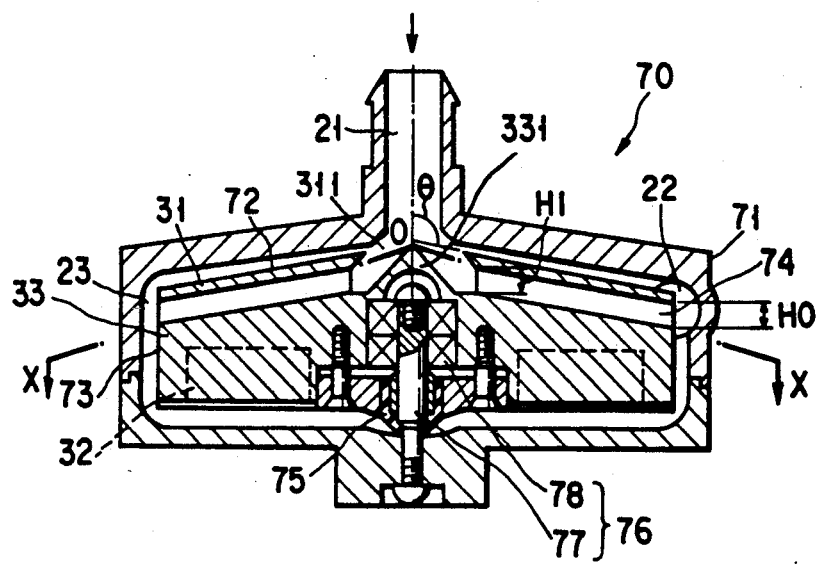
FIG. 9 is a longitudinal sectional view of a blood pump according to the third embodiment of the present invention.
Figure 10:
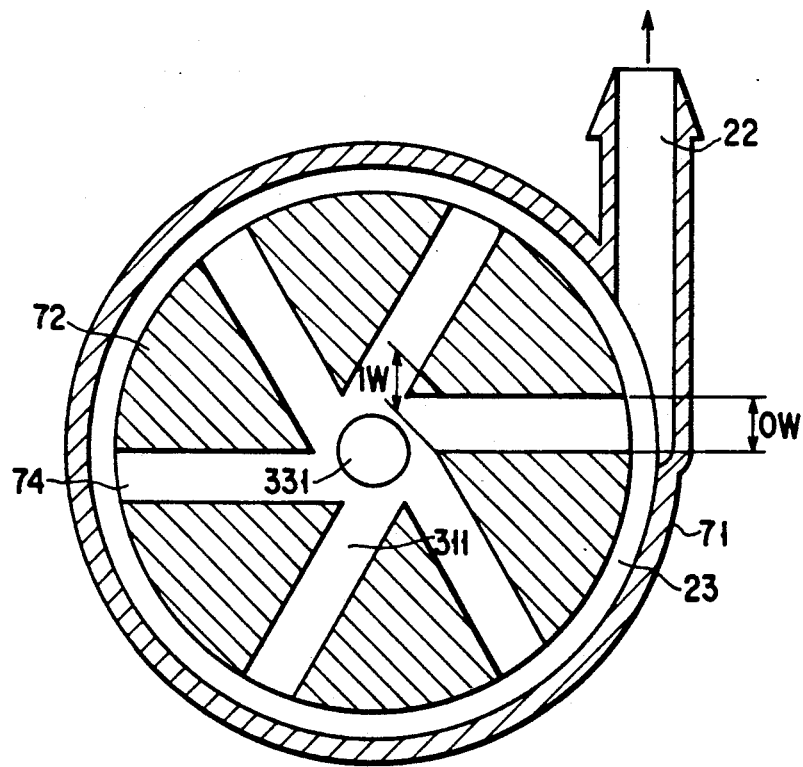
FIG. 10 is a cross-sectional view of the blood pump of the third embodiment taken along line X-O-X in FIG. 9.

A blood pump according to the third embodiment of the present invention will be described with reference to FIGS. 9 and 10. The same reference numerals as in the first and second embodiments denote the same parts in the third embodiment, and a detailed description thereof will be omitted.

The pump 70 of the third embodiment is substantially the same as the pump 50 of the second embodiment. A cover 31 and a shroud 73 will be formed integrally with each other to constitute a rotator 72, if an inclined portion will be formed as an escape taper for molding.

In addition, since the rotator 72 of the pump 70 of the third embodiment is made of an integral body, the blood path is seamless to rarely cause thrombus.

A detailed arrangement of the blood pump 70 of the third embodiment will be described below.

In a seal mechanism 76 of the third embodiment, a bearing 78 is mounted at an upper end portion of a shaft 77.

In a housing 71 of the third embodiment, the proximal portion of the blood outlet 22 slightly extends outward.

Third Embodiment

Housing

| Material | Acrylic resin |
|---|---|
| Inner Diameter of Housing | 84 mm |
| Amount of Filled Blood | 47 cc |
| Inner Diameter of Blood Inlet | 8 mm |
| Inner Diameter of Blood Outlet | 8 mm |

Rotator

| Material | Polycarbonate resin |
|---|---|
| Outer Diameter | 78 mm |
| Inner Diameter of Blood Flow Inlet | 19 mm |
| Number of Liquid Paths (radially arranged at equal angular intervals) | 6 |
| Cross-sectional Area of Inlet Opening of Liquid Path | 28.1 mm² (IH 3.7 mm × IW 7.6 mm) |
| Cross-sectional Area of Outlet Opening of Liquid Path | 38.7 mm² (OH 4.5 mm × OW 8.6 mm) |
| Angle θ between Central Axis of Liquid Path and Central Axis of Inlet Port | 100° |
| Angle between Inclined Surface of Projection and Central Axis | 45° |
| Diameter of Bottom Portion of Projection | 10 mm |
| Driven Magnet | 6-pole magnetized ferrite magnet (outer diameter: 70 mm; inner diameter: 32 mm; and thickness: 8 mm) |

External Drive Unit

The same as the first embodiment.

Measurement of Pump Characteristics

A glycerin solution of which viscosity was 4 c.p., was transported using the blood pumps 10 and 50 of the first and second embodiments, and their pump characteristics were measured. The measurement was performed by changing the pump speeds and pump flow rates. The results are shown in FIG. 4 (first embodiment) and FIG.

7 (second embodiment). As is apparent from FIGS. 4 and 7, both the blood pumps 10 and 50 exhibited good pumping characteristics.

Figure 5:
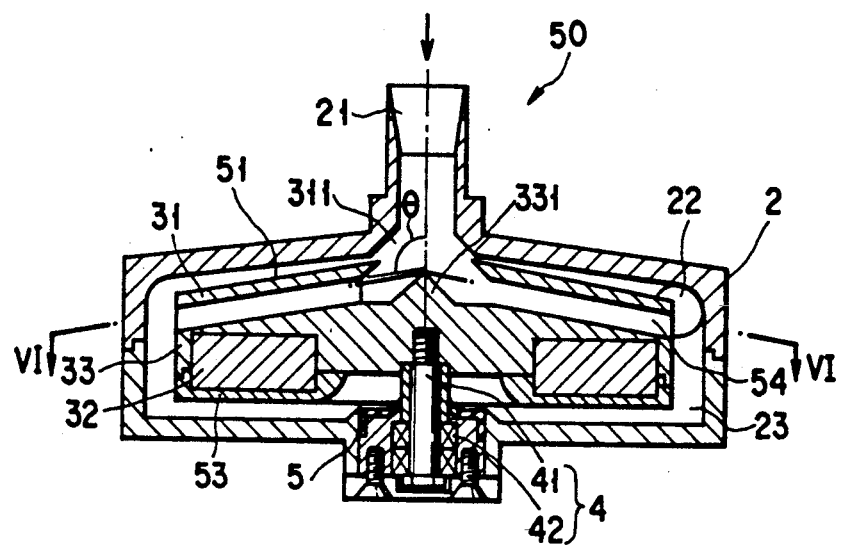
FIG. 5 is a longitudinal sectional view of a blood pump according to the second embodiment of the present invention.
Figure 6:
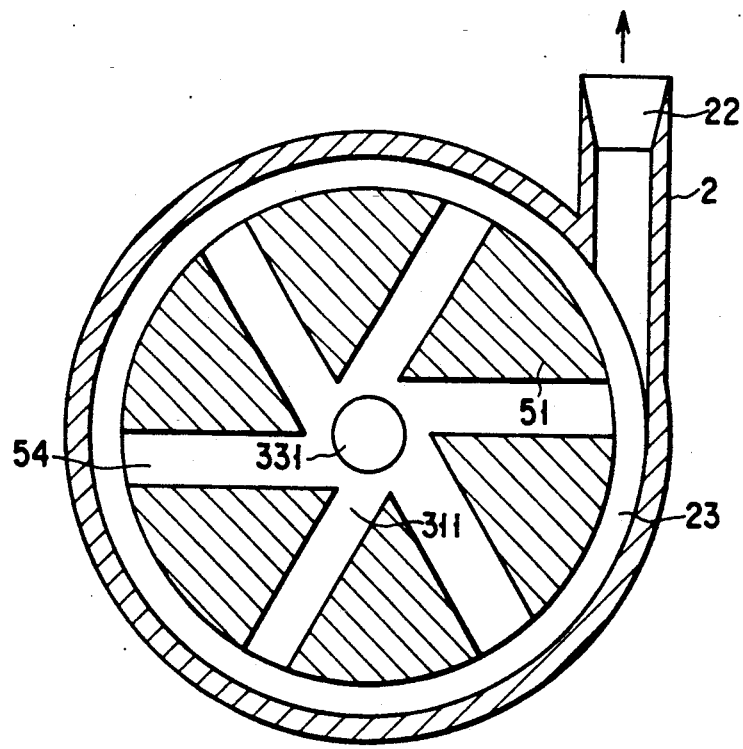
FIG. 6 is a cross-sectional view of the second pump of the second embodiment when taken along a rotator (VI—VI in FIG. 5)

The present invention is not limited to the pump 10 arranged such that the blood paths 34 are arcuated and their cross-sectional areas are monotonously decreased, as shown in FIG. 1, and the pump 50 arranged such that the liquid paths 54 are straight and their cross-sectional areas are almost constant along the blood flows in the paths 54, as shown in FIG. 5. The same effects as described above can be obtained in a pump arranged such that the liquid paths are straight and their cross-sectional areas are monotonously decreased, or in a pump arranged such that the liquid paths are arcuated and their cross-sectional areas are kept almost constant.

The bearing structures are not limited to the ones shown in FIGS. 1 and 5. For example, the shaft 41 may be fixed in the housing 2, or the bearing 42 and the seal unit 5 may be arranged in the shroud 33 (as shown in FIG. 9). In addition, the driving unit and the driven unit may be directly connected to each other without magnetic coupling.

A liquid to be transported is not limited to blood. As long as a liquid contains a material which tends to be denatured by heat, the present invention is applicable to any such liquid.

Since a liquid pump according to the present invention is arranged as described above, the liquid supplied from the liquid inlet passes through a liquid flow portion of a rotator and then passes through a plurality of radial liquid paths, thereby receiving a centrifugal force. The liquid is then delivered from the liquid outlet. At this time, since the liquid paths are formed such that their cross-sectional areas are kept almost constant or monotonously decreased along the fluid flows in the paths, the resultant liquid flows become substantially constant-speed flows or accelerated flows, and the flows tend not to be separated from the walls of the liquid paths, thereby preventing turbulence without increasing the amount of the liquid filled in the pump. Therefore, damage to the solid components in blood can be prevented. In addition, if the liquid paths are straight, the amount of a body fluid filled in the pump can be further reduced without degrading the pump characteristics. Since the central axis of each liquid path forms an angle $\theta$ falling within the range of about 90° to 105° with respect to the central axis of the rotators, bubbles can be effectively removed without degrading the pumping characteristics.

As has been described above, a liquid pump apparatus according to the present invention has a liquid inlet and a liquid outlet. The pump apparatus comprises a housing having an almost cylindrical chamber therein, a plurality of radial liquid paths, a rotator rotatably mounted in the housing, and a bearing for rotatably supporting the rotator. In this pump apparatus, the liquid paths are formed such that their cross-sectional areas are almost constant or reduced along the liquid flows in the paths. The liquid supplied from the liquid inlet passes through the liquid flow portion of the rotator and then passes through the plurality of radial liquid paths, thereby receiving a centrifugal force. The liquid is then delivered from the liquid outlet. At this time, since the liquid paths are formed such that their cross-sectional areas are almost constant or monotonously reduced along the liquid flows in the paths, the resultant liquid flows become substantially constant-speed liquid flows or accelerated liquid flows. As a result, the flow is rarely separated from the walls of the liquid paths, the turbulence can be prevented without increasing the amount of the liquid filled in the pump, and the damage to the solid components in the blood can be prevented. In addition, if the liquid paths are straight, the amount of the liquid filled in the pump can be further reduced without degrading the pumping characteristics. Since the central axis of each liquid path forms an angle $\theta$ falling within the range of about 90° to 105° with respect to that of the rotator, bubbles can be effectively removed without degrading the pumping characteristics.

Figure 12:
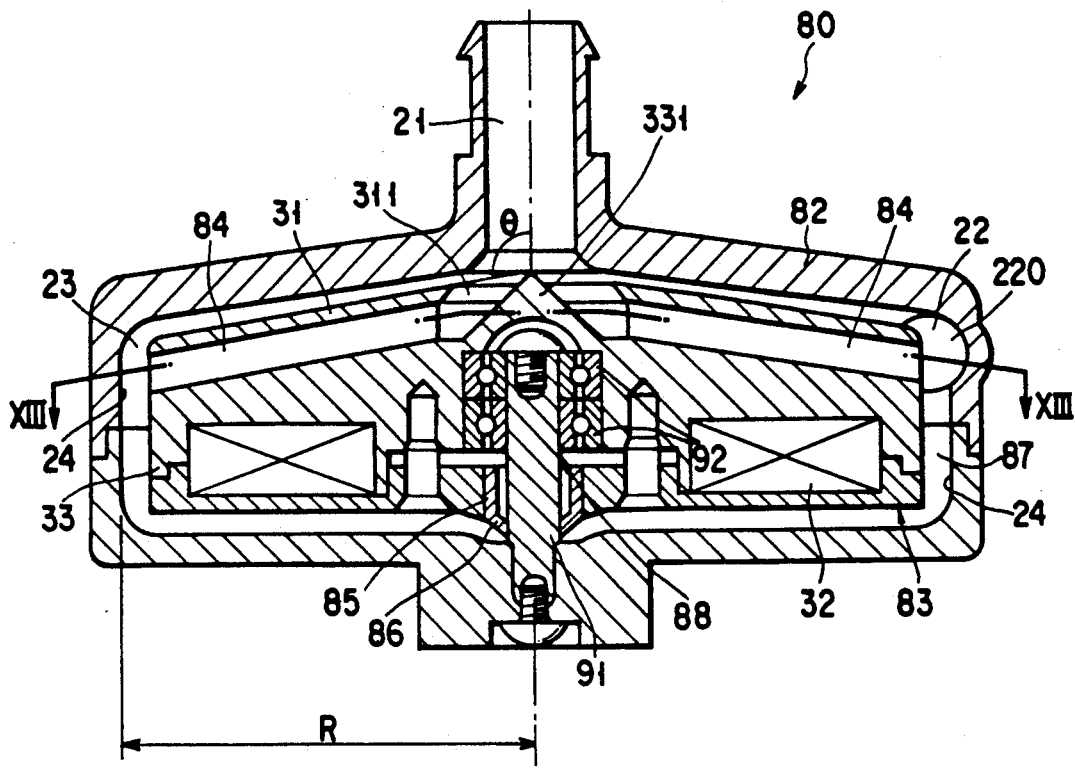
FIG. 12 is a vertical cross sectional view showing a blood pump according to the fourth embodiment of the present invention.
Figure 13:
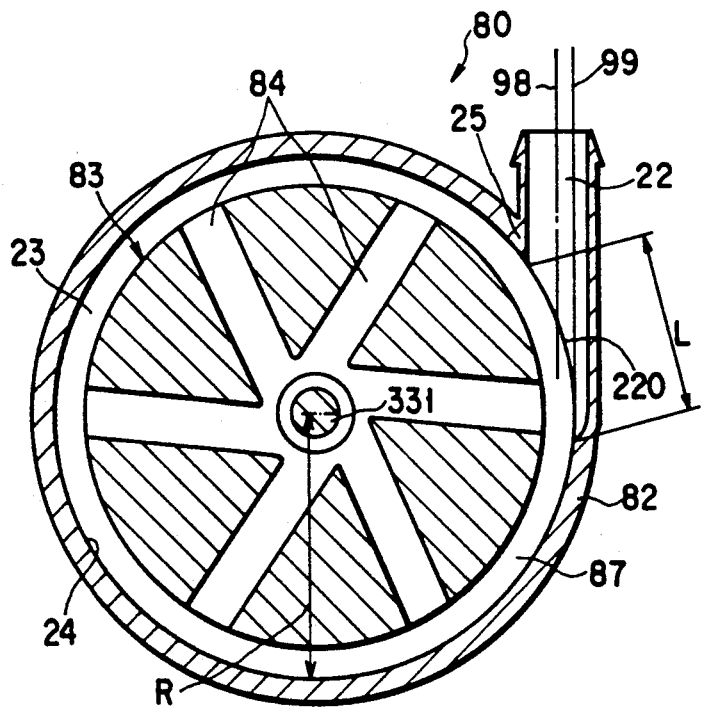
FIG. 13 is a longitudinal cross sectional view, partly broken away, showing the rotator included in the blood pump according to the fourth embodiment of the present invention (XIII—XIII in FIG. 12)

FIG. 12 is a vertical cross sectional view showing the construction of a blood pump according to each of the fourth embodiment of the present invention. FIG. 13 is a longitudinal cross sectional view along the line A—A shown in FIG. 12.

A flat disk-like rotator 83, which is concentric with the chamber 23, is rotatably arranged within the chamber 23 of the housing 82 of the blood pump 80. The rotator 83 comprises a plate-like cover 31 and a shroud 33. A disk-like driven magnet 32 magnetized to form a plurality of magnetic poles is embedded i the shroud 33. As shown in FIG. 13, six tubular blood paths 84 are formed between the cover 31 and the shroud 33 such that these blood paths extend radially from the central portion of the rotor 3. Where the cover 31 and the shroud 33 are formed of separate members, grooves are formed in the upper portion of the shroud 33. Also, the upper openings of these grooves are shielded by the cover 31 so as to form the tubular blood paths 84.

Various hard resins can be used for forming each of the housing 82, the cover 31 and the shroud 33. The hard resins used for forming these members include, for example, a hard polyvinyl chloride, polyethylene, polypropylene, polystyrene, polycarbonate, acrylic resins such as acryl resin and polymethyl methacrylate (PMMA), polyesters such as polyethylene terephthalate (PET) and polybutylene terephthalate (PBT), polysulfones and polyacrylates. It is particularly desirable to use polycarbonate and an acrylic resin because these resins are not poisonous, and are excellent in compatibility with blood, transparency and moldability.

The cover 31 is provided with a circular opening 311 serving to guide the blood, which is introduced into the housing 82 through the blood inlet port 21, to the blood paths 84.

Each of the blood paths 84 extends substantially linearly from the central portion of the rotor 3 toward the outer circumferential surface. Also, each blood path 84 is rectangular in cross section and has a substantially uniform cross sectional area in the blood flowing direction within the blood path. The particular construction permits a substantially uniform flow rate of the blood within the blood path 84, with the result that an eddy flow is unlikely to take place. Since it is possible to suppress the eddy flow, which causes a turbulent flow of the blood, hemolysis can be prevented in the present invention. Specifically, the cells in the blood are prevented from being destroyed or damaged. Of course, the function of the cells is prevented from being lowered. What should also be noted is that, since the blood path is straight, the priming volume can be decreased without deteriorating the pumping characteristics.

As described above, the blood path 84 has a substantially uniform cross sectional area in the blood flowing direction. This technical idea covers the case where a slight tapering is formed in the inner surface of the blood path 84, as far as the blood flow rate, or the blood velocity, is substantially constant within the blood path 84.

Where the cover 31 and the shroud 33 are formed integrally to provide the rotator 83, a gradient of about 1° may be formed on the inner surface of the blood path 84 as a draft angle used in the step of forming the blood path 84. The performance in this case is substantially equal to that in the case where the cross sectional area of the blood path 84 is constant over the entire region including the inlet port and the outlet port of the blood path 84. Where the rotator 83 is integrally formed, the inner surface of the blood path 84 is made seamless, leading to an advantage that a thrombus is unlikely to be generated.

The cross sectional shape of the blood path need not be not restricted to a rectangular cross section. For example, it is possible for the blood path to have a circular, elliptical, semicircular or polygonal cross section other than rectangular cross section. Also, the number of blood paths formed in the rotator 83 is not particularly restricted in the present invention, though about 2 to 12 blood paths are generally formed, and it is desirable to form about 4 to 8 blood paths in the rotator 83.

The cross sectional area of a single blood path 84 is not particularly restricted in the present invention, though the blood path 84 has in general about 10 to 100 mm² of a cross sectional area and should desirably have a cross sectional area of about 20 to 50 mm². The number of blood paths and the cross sectional area of each of the blood paths described above make it possible to decrease the priming volume and to improve the pumping efficiency.

In the present invention, it is possible for the blood path 84 to be formed such that the cross sectional area of the blood path is gradually diminished continuously along the blood flow with in the path. In this case, the blood velocity is increased with increase in the distance from the center of the rotator 83, with the result that the turbulent flow of the blood is suppressed so as to prevent the cells within the blood from being destroyed and to prevent the function of the cells from being lowered. The reduction rate A ($=OA/IA \times 100$) of the cross sectional area of the blood path, i.e., the ratio in the cross sectional area OA of the outlet port to the cross sectional area IA of the inlet port, is not particularly restricted in the present invention, though the reduction rate Q falls in general within a range of between 30 and 100% and should desirably fall within a range of between 50 and 80%.

Where the blood path 84 has a rectangular cross section, the gradual reduction of the cross sectional area toward the outlet port can be achieved by gradually diminishing the height and/or width of the rectangular cross section. Where the blood path has a circular, elliptical, or semicircular cross section, the reduction in the cross sectional area can be achieved by gradually diminishing the diameter of the cross sectional shape toward the outlet port.

It is desirable to form the blood path 84 such that the central axis makes an angle $\theta$ of about 90° to 105°, particularly 97° to 103°, with the axis of the rotator 83 (downward of the projection 36 in the drawing). In the embodiment of FIG. 12, said angle $\theta$ is about 100°. It is desirable to form the blood path 84 such that the lower surface (or bottom of groove) makes an angle of about 90° to 105°, particularly 97° to 103°, with the axis of the rotator 83. Where the blood path is formed in this fashion, the bubbles within the blood positioned in the blood path rise along the inner surface of the cover 31 to reach the opening 311 in the step of loading the blood into the chamber 23. It follows that these bubbles can be removed easily through the blood inlet port 21 It is desirable for the angle made between the blood path 84 and the axis of the rotator 83 to be equal in respect of all of the blood paths.

Furthermore, it realizes to improve pump characteristics and to decrease hemolysis.

A conical projection 331 projecting toward the blood inlet port 21 is formed in that portion of the center of rotation of the shroud 33 which faces the opening 311. The blood introduced through the blood inlet port 21 and passing through the opening 311 is radially divided by the projection 331 to form separate flows. It should be noted that the projection 331 permits uniformly and effectively distributing the blood passing through the opening 311 to the blood paths 84 so as to improve the pumping efficiency.

It is desirable for the outer circumferential surface of the projection 331 to make an angle of about 10° to 80°, particularly about 30° to 60°, with the axis of the rotator 83. Further, the projection 331 should desirably have a maximum diameter in the bottom portion of about 25 to 100%, more desirably about 50 to 90%, based on the diameter of the opening 311, and should desirably have a height of about 1 to 20 mm, particularly about 2 to 10 mm. Incidentally, the shape of the projection 331 need not be restricted to a conical shape as shown in the drawing. For example, it is acceptable for the projection 331 to be shaped bullet-like, semispherical, etc.

The rotator 83 is rotatably supported within the housing 82 by a bearing portion 88 which comprises a shaft 91 fixed to the bottom of the housing 82 and two bearings 92 disposed within the shroud 33. The bearings 92 are embedded in the center of the shroud 33, and the shaft 91 is inserted into the inner space of the bearings 92. It is desirable to use, for example, a ball bearing, a roller bearing, etc. as the bearing 92. It is also acceptable to use a sliding bearing as the bearing 92.

A ring-like sealing member 85 is fixed to the outer circumferential surface of the shaft 91 at the bottom of the shroud 33. During rotation of the rotator 83, a lip portion 86 at the lower end of the sealing member 85 is brought into a sliding contact with the outer circumferential surface of the shaft 91 so as to achieve sealing between the inner space of the chamber 23 and the inner space of the shroud 33.

The sealing member 85 id formed of, for example, various soft resins such as polybutadiene, polyisoprene and polyisobutylene and various elastomers such as silicone rubber, fluorine rubber, natural rubber and polyurethane. It is particularly desirable to use silicone rubber, fluorine rubber and polyurethane elastomers for forming the sealing member because generation of a frictional heat caused by the sliding between the sealing member and the shaft 91 can be suppressed so as to effectively prevent the blood from being denatured or coagulated locally.

The sealing mechanism employed in the present invention need not be restricted to the lip sealing member 85 shown in the drawing. For example, it is also possible to employ a face sealing using an elastic body and a counter face or a mechanical sealing using a sliding member and a counter face.

The construction of the bearing portion 84 need not be restricted to that shown in the drawing. For example, the bearing portion may also be constructed such that the shaft 91 is fixed to the shroud 33, the bearing 92 is mounted at the bottom of the housing 82, and the bearing 9 is shielded from within the chamber 23 by a predetermined sealing mechanism.

The present invention is featured in the circumferential length of the opening 200 communicating with the inner circumferential surface 24 of the housing at the blood inlet port 22. To be more specific, the relationship $L \geq 0.4 R$, preferably $R \geq L \geq 0.5 R$, is satisfied in the present invention, where L denotes the length of chord of contact with the opening 220, said opening 220 communicating with housing inner surface 24, and R represents the radius of the chamber 23 (or inner radius of the housing 2).

Where the circumferential length L of the opening 220 is less than 0.4 R, the blood tends to stagnate or form a turbulent flow within the space 87 formed between the housing inner surface 24 and the outer circumferential surface of the rotator 83, leading to a low pumping efficiency. In this case, hemolysis is likely to take place.

Where the relationship between L and R falls within the range defined in the present invention, the area of the opening 220 is sufficiently large, making it possible to guide smoothly the blood within the space 87, within which the pressure is increased by the blood inflow through the blood path 84, to the blood outlet port 22 for the discharge. Since generation of a turbulent flow of the blood is markedly suppressed around the opening 220 as described above, it is possible to suppress hemolysis and to improve the pumping efficiency. As a result, a high pump head (discharge amount) can be obtained with a low rotation speed. It follows that the hemolysis can be suppressed more effectively. Further, the blood is more effectively prevented from being denatured or coagulated by the frictional heat generated between the shaft 91 and the lip portion 86. What should also be noted is that the improvement in the pumping efficiency permits miniaturizing the pump, with the result that the priming volume can be further diminished.

The relationship between L and R can be determined to fall within the range defined in the present invention by increasing the inner diameter of the blood outlet port 22 or by adjusting the positional relationship between the blood outlet port 22 and the chamber 23 to ensure a large value of L. In the present invention, it is desirable to adjust the positional relationship because it is important to prevent increase in the priming volume. Specifically, it is desirable for a tangential line 99 parallel with the axis 98 of the blood outlet port 22 to extend within the blood outlet port 22. It should be noted that the tangential line 99 is in contact with the inner circumferential surface 24 of the housing 82. In order to meet the relationship between L and R defined in the present invention, it is also desirable to cut off smoothly an edge portion 25 of the housing 82 so as to increase the value of L.

For driving the blood pump 80 of the construction described above, an external driving means (not shown) is mounted to the bottom portion of the housing 82. For example, the external driving means includes a motor and a driving magnet magnetized to form a plurality of magnetic poles and coaxially fixed to the shaft of the rotor of the motor. The driving magnet is mounted to face the driven magnet 32 housed in the blood pump 80 such that a mutual attractive force is generated between the driving magnet and the driven magnet.

When the motor is rotated, the driving magnet is also rotated, with the result that the rotational force is transmitted to the driven magnet in a non-contact manner so as to rotate the rotator 83 in a counterclockwise direction in FIG. 13. The rotation of the rotator 83 causes the blood introduced into the housing 82 through the blood inlet port 21 is distributed and guided into each of the blood paths 84. Then, the blood receives a centrifugal force so as to flow within each blood path 84 toward the outer circumferential region of the rotator 83. The blood further flows out of the blood paths 84 to enter the space 87 and, then, is discharged through the blood outlet port 22.

It is possible for the external driving means to be formed of a flat stator coil alone. In this case, a flat brushless motor structure directly driven by the stator coil is employed in the driven magnet 32. Further, the mutual attractive force between the driving magnet and the driven magnet is employed for the torque transmission to the rotator 83 in the embodiment described above. However, it is also possible to employ a removable coupling mechanism between the rotary shaft of the rotator 83 and the driving shaft on the side of the external driving means for the torque transmission.

Further, a driving means (motor) may be housed in the blood pump 80 in place of using the external driving should be directly joined to the rotary shaft of the rotator 83.

It is desirable for the blood pump of the present invention to be used in external blood circulation devices such as Extracorporeal Membrane Oxygenator (ECMO), Emergency Bypass System (EBS), Left Ventricular Bypass (LVB), and Ventricular Assist Device (VAD), which are used in the heart operation of respiratory disease.

The blood pump of the present invention can also be used for transportation of body fluids (physiological fluids) such as plasma or serum. Furthermore, the pump can be used for transportation other body fluids containing substances which are likely to be denatured by heat.

A detailed arrangement of the blood pump 80 of the fourth embodiment will be described below.

Fourth Embodiment

Housing

| Material | Acrylic resin |
| --- | --- |
| Radius R of the Chamber | 42 mm |
| Priming Volume | 47 ml |
| Inner Diameter of the Blood Inlet Port | 8 mm |
| Inner Diameter of the Blood Outlet Port | 8 mm |
| Circumferential Length L of the Opening of the Blood Outlet Port | 24 mm (L = 0.57R) |
| Distance between the Axis of the Blood Outlet Port and the Center of the Housing | 39 mm |

Rotator

| Material | Polycarbonate resin |
| --- | --- |
| Radius | 37 mm |
| Opening Diameter of the Cover | 19 mm |
| Shape of Blood Path | Straight |
| The Number of Blood Paths | 6 (arranged to make an equal angle) |

-continued

| Material | Polycarbonate resin |
|---|---|
| Cross-sectional Area of Blood Path | 32 mm² (uniform over the entire lengthwise region of the blood path) |
| Angle θ Formed between Central Axis of the Blood Path and Central Axis of Inlet Port | 100° |
| Angle Formed between the Outer Circumferential Surface of Projection and Axis of the Rotator: | 45° |
| Diameter in the Bottom Portion of Projection: | 15 mm |
| Driven Magnet | Ring-like ferrite magnet magnetized to form 6 magnetic poles |
| Size of Driven Magnet | 70 mm (outer diameter); 32 mm (inner diameter); 8 mm (thickness) |

External Driving Apparatus

| Motor | Brushless DC motor (90W) |
|---|---|
| Driving Magnet | Ring-like ferrite magnet magnetized to form 6 magnetic poles |
| Size of Driving Magnet | 70 mm (outer diameter); 32 mm (inner diameter); 10 mm (thickness) |
| Distance between Driving Magnet and Driven Magnet | 8.5 mm |

Second Control

A blood pump was prepared as in the fourth embodiment, except that the conditions of the housing were set as follows:

Housing

| Material | Acrylic resin |
|---|---|
| Radius R of the Chamber | 42 mm |
| Priming Volume | 47 ml |
| Inner Diameter of the Blood Inlet Port: | 8 mm |
| Inner Diameter of the Blood Outlet Port: | 8 mm |
| Circumferential Length L in the Opening of the Blood Outlet Port | 16 mm (L = 0.38R) |
| Distance between the Axis of the Blood Outlet Port and the Center of the Housing | 37 mm |

Measurement of the Pump Characteristics

A glycerine solution having a viscosity of 4 cP was pumped by using the blood pump for each of the fourth embodiment of the present invention and control 2 so as to measure the discharge pressure of the pump, i.e., pump head in terms of mmHg. The experiment was conducted by changing the pump flow rate (liters/min) under the pump speed of 1000, 1500, 2000, 2500 and 3000 rpm. FIG. 14 shows the results in the case of using the blood pump for the fourth embodiment of the present invention. The results in the case of using the blood pump for second control are shown in FIG. 15.

As apparent from comparison between FIGS. 14 and 15, the blood pump for the fourth embodiment of the present invention permits a high pump head and excellent pump characteristics in each of the rotation speed of the pump, compared with the blood pump for second control.

As described above in detail, the blood pump according to the present invention makes it possible to prevent the cells of the blood from being destroyed and prevent the function of the cells from being lowered during transportation of the blood. In addition, the blood pump of the present invention exhibits excellent pump characteristics under a low rotation speed.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept a defined by the appended claims and their equivalents.

What is claimed is:

1. A centrifugal type blood pump apparatus for blood components, comprising:
a housing forming a substantially cylindrical liquid chamber;
an inlet port formed at an upper central portion of said housing and communicating with both a supply source of blood component and said chamber;
an outlet port formed in a peripheral portion of said housing and communicating with said chamber, said outlet port comprising an opening in said housing;
a rotator rotatably arranged in said chamber and having an upper cover and a lower shroud, a lower surface of the upper cover being inclined such that an angle θ formed by the lower surface and a central axis of the inlet port is an obtuse angle, and a plurality of grooves formed radially in an upper portion of said shroud;
projection means formed at an upper central portion of the shroud and located immediately below said inlet port for directing input blood component toward said plurality of grooves;
bearing means for rotatably supporting the rotator with respect to the housing;
motor means for applying a rotational force to the rotator to rotate the rotator; and
a plurality of distributing paths defined between said upper cover and said plurality of grooves of the shroud, and communicating with both the inlet port and the outlet port, said distributing paths each having at least a surface which is downwardly inclined from said inlet port toward said outlet port and said distributing paths being separated from each other and out of communication with each other at portions thereof between input and output ends thereof and, each of said distributing paths having a cross sectional area which gradually diminishes in one direction along the length thereof.

2. The blood pump apparatus according to claim 1, wherein each of said distributing paths is bent.

3. The blood pump apparatus according to claim 1, wherein each of said distributing paths is straight.

4. The blood pump apparatus according to claim 1, wherein said angle θ is over 90° and less than 105°.

5. The blood pump apparatus according to claim 1, wherein said upper portion of said shroud is inclined from a center thereof toward the periphery thereof so as to make an obtuse angle with said inlet port, such that each of said distributing paths is downwardly inclined, and an outlet of each of said distributing paths is positioned lower than an inlet of the respective distributing path.

6. The blood pump apparatus according to claim 1, wherein said opening of the outlet port satisfies the condition of $L \geq 0.4\,R$, where L denotes a length of a chord of contact with said opening communicating with the chamber, and R represents the radius of the chamber.

7. The blood pump apparatus according to claim 1, wherein said downwardly inclined surfaces of said distributing paths comprises an upper surface thereof.

8. The blood pump apparatus according to claim 2, wherein said angle $\theta$ is over 90° and less than 105°.

9. The blood pump apparatus according to claim 3, wherein said angle $\theta$ is over 90° and less than 105°.

10. A centrifugal type blood pump apparatus for blood components, comprising:
   a housing forming a substantially cylindrical liquid chamber;
   an inlet port formed at an upper central portion of said housing and communicating with both a supply source of blood component and said chamber;
   an outlet port formed in a peripheral portion of said housing and communicating with said chamber, said outlet port defining an opening in said housing;
   a rotator arranged in said chamber and having an upper cover and a lower shroud;
   a projection formed at an upper central portion of the shroud and located immediately below said inlet port;
   bearing means for rotatably supporting the rotator with respect to the housing;
   motor means for applying a rotational force to the rotator;
   a plurality of grooves being formed radially in the upper surface of said shroud; and
   a plurality of distributing paths defined between said plurality of grooves and said cover and communicating with both the inlet port and the outlet port, wherein said opening of said outlet port satisfies the condition of $L \geq 0.4\,R$, where L denotes a length of a chord of contact with said opening communicating with the chamber, and R represents the radius of the chamber.

11. The blood pump apparatus according to claim 10, wherein each of said distributing paths has a cross sectional area which is substantially constant over the entire length region thereof.

12. The blood pump apparatus according to claim 10, wherein each of said distributing paths has a cross sectional area which gradually diminishes in one direction along the length thereof.

13. The blood pump apparatus according to claim 10, wherein each of said distributing paths is downwardly inclined.

14. The blood pump apparatus according to claim 10, wherein said distributing paths are separated from each other and are out of contact with each other along the lengths thereof between input and output ends thereof.

15. A centrifugal blood pump apparatus for blood components, comprising:
   a housing forming a substantially cylindrical liquid chamber;
   an inlet port formed at an upper central portion of said housing and communicating with both a supply source of blood component and said chamber;
   an outlet port formed in a peripheral portion of said housing and communicating with said chamber, said outlet port defining an opening in said housing;
   a rotator arranged in said chamber and having an upper cover and a lower shroud, a lower surface of the upper cover being inclined such that an angle $\theta$ formed by the lower surface and a central axis of the inlet port is an obtuse angle, and a plurality of grooves being formed radially in an upper portion of said shroud;
   a projection formed at an upper central portion of the shroud and located immediately below said inlet port;
   bearing means for rotatably supporting the rotator with respect to the housing;
   motor means for applying a rotational force to the rotator; and
   a plurality of distributing paths defined between said upper cover and said plurality of grooves of the shroud, and communicating with both the inlet port and the outlet port;
   wherein said opening of said outlet port satisfies the condition of $L \geq 0.4\,R$, where L denotes a length of a chord of contact with said opening communicating with the chamber, and R represents the radius of the chamber.

16. The blood pump apparatus according to claim 15, wherein each of said distributing paths has a cross sectional area which is substantially constant over the entire length region thereof.

17. The blood pump apparatus according to claim 15, wherein each of said distributing paths has a cross sectional area which gradually diminishes in one direction along the length thereof.

18. The blood pump apparatus according to claim 15, wherein each of said distributing paths is downwardly inclined.

19. The blood pump apparatus according to claim 15, wherein said distributing paths are separated from each other and are out of contact with each other along the lengths thereof between input and output ends thereof.

20. A centrifugal type blood pump apparatus for blood components, comprising:
   a housing forming a substantially cylindrical liquid chamber;
   an inlet port formed at an upper central portion of said housing and communicating with both a supply source of blood component and said chamber;
   an outlet port formed in a peripheral portion of said housing and communicating with said chamber, said outlet port comprising an opening in said housing;
   a rotator rotatably arranged in said chamber and having an upper cover and a lower shroud, a lower surface of the upper cover being inclined such that an angle $\theta$ formed by the lower surface and a central axis of the inlet port is an obtuse angle, and a plurality of grooves being formed radially in an upper portion of said shroud;
   projection means formed at an upper central portion of the shroud and located immediately below said inlet port for directing input blood component toward said plurality of grooves;
   bearing means for rotatably supporting the rotator with respect to the housing;

motor means for applying a rotational force to the rotator to rotate the rotator; and a plurality of distributing paths defined between said upper cover and said plurality of grooves of the shroud, and communicating with both the inlet port and the outlet port, said distributing paths each having at least a surface which is downwardly inclined from said inlet port toward said outlet port and said distributing paths being separated from each other and out of communication with each other at portions thereof between input and output ends thereof, and each of said distributing paths having a cross sectional area which is substantially constant over the entire length thereof.

21. The blood pump apparatus according to claim 20, wherein each of said distributing paths is bent.

22. The blood pump apparatus according to claim 20, wherein each of said distributing paths is straight.

23. The blood pump apparatus according to claim 20, wherein said angle $\theta$ is over 90° and less than 105°.

24. The blood pump apparatus according to claim 20, wherein said upper portion of said shroud is inclined from a center thereof toward the periphery thereof so as to make an obtuse angle with said inlet port, such that each of said distributing paths is downwardly inclined, and an outlet of each of said distributing paths is positioned lower than an inlet of the respective distributing path.

25. The blood pump apparatus according to claim 20, wherein said opening of the outlet port satisfies the condition of $L \geqq 0.4 R$, where L denotes a length of a chord of contact with said opening communicating with the chamber, and R represents the radius of the chamber.

26. The blood pump apparatus according to claim 20, wherein said downwardly inclined surfaces of said distributing paths comprises an upper surface thereof.

27. The blood pump apparatus according to claim 21, wherein said angle $\theta$ is over 90° and less than 105°.

28. The blood pump apparatus according to claim 22, wherein said $\theta$ is over 90° and less than 105°.

* * * * *